United States Patent [19]

Plechinger et al.

[11] Patent Number: 5,259,842
[45] Date of Patent: Nov. 9, 1993

[54] HIGH-PRESSURE LIQUID DISPENSER FOR THE DISPENSING OF STERILE LIQUID

[75] Inventors: Hans Plechinger, Neusäss; Josef Köhler, Aachen, both of Fed. Rep. of Germany

[73] Assignee: HP-Media Gesellschaft MgH fur Medizintechnische Systeme, Fed. Rep. of Germany

[21] Appl. No.: 7,919

[22] Filed: Jan. 22, 1993

[30] Foreign Application Priority Data

Jan. 25, 1992 [DE] Fed. Rep. of Germany ....... 4201992

[51] Int. Cl.5 .......................... A61M 1/00; A61M 3/00
[52] U.S. Cl. ..................................... 604/152; 604/43; 222/334; 222/389
[58] Field of Search ............... 604/131, 138, 150, 152, 604/35, 22, 43, 39, 232, 226; 606/190; 417/474; 222/334, 389, 326, 327

[56] References Cited

U.S. PATENT DOCUMENTS

| | | |
|---|---|---|
| 3,087,433 | 4/1963 | Cerveny . |
| 3,221,947 | 12/1965 | Penn .................. 222/389 |
| 3,507,278 | 4/1970 | Werding . |
| 3,984,034 | 10/1976 | Cohen ................. 222/389 |
| 4,335,835 | 6/1982 | Beigler et al. ....... 604/131 |
| 4,634,027 | 1/1987 | Kanarvogel ......... 222/389 |
| 4,635,827 | 1/1987 | Rocdig ................ 222/389 |
| 4,690,672 | 9/1987 | Jeltrup ................. 604/43 |
| 4,715,848 | 12/1987 | Beroza ................ 604/43 |
| 4,972,969 | 11/1990 | Randklev ............ 222/326 |
| 5,147,311 | 9/1992 | Pickhard ............. 604/131 |

FOREIGN PATENT DOCUMENTS

| | | |
|---|---|---|
| 0232678 | 8/1986 | European Pat. Off. . |
| 2447513 | 10/1974 | Fed. Rep. of Germany . |
| 3019115 | 5/1980 | Fed. Rep. of Germany . |
| 3421390 | 6/1984 | Fed. Rep. of Germany . |
| 3812841 | 4/1988 | Fed. Rep. of Germany . |
| 4018736 | 6/1990 | Fed. Rep. of Germany . |
| 4022379 | 7/1990 | Fed. Rep. of Germany . |
| 2324898 | 9/1976 | France . |
| 1639421 | 6/1986 | U.S.S.R. . |
| 1569019 | 2/1988 | U.S.S.R. . |

*Primary Examiner*—John G. Weiss
*Attorney, Agent, or Firm*—Ostrolenk, Faber, Gerb & Soffen

[57] ABSTRACT

A high pressure liquid dispenser for the delivering preferable sterile liquid with high pressure to a catheter. The dispenser includes a flexible or weak wall storage container in which the liquid to be dispensed is stored and a conduit from the front end wall of that container for dispensing liquid to a catheter. A pressure container around the storage container is stiff enough to take up the pressure of the liquid and the deformation of the storage container, so that the pressure of the liquid elevated by the pump piston may be substantially greater than without the protective pressure container around the storage container. A fluid actuated drive acts on the pump piston. The piston of the fluid actuated drive and the pump piston are respectively so shaped as to provide a pressure boost for producing higher pressure in the liquid in the storage container to produce the jet.

26 Claims, 2 Drawing Sheets

HIGH-PRESSURE LIQUID DISPENSER FOR THE DISPENSING OF STERILE LIQUID

BACKGROUND OF THE INVENTION

The present invention relates to a high-pressure liquid dispenser for dispensing sterile liquid at high pressure through a catheter to an organ in a body for breaking the object into small parts and removing them parts thereafter.

In organs of humans and animals, and particularly their arteries, veins, liver and kidneys, vascular constrictions (for instance, tumors, deposits of lime, embolisms, etc.) or foreign bodies (gallstones, kidney stones, tumors) may occur. The inventors have developed a catheter which can be inserted into the organ to be treated. By means of the catheter, the constriction of the vessel or the foreign body can be removed or crushed within the organ in question by a sharp jet of liquid and can thereby be broken into small particles which are transported by the jet of liquid out of the organ through the catheter. In order that the jet of liquid may be active in this manner, it must have a pressure of at least 2 bar. The pressure has an upper limit determined by the compressive strengths of the catheter and of the liquid conduits and may amount, for instance, to up to 130 bar. Conduits in which such high pressures prevail should be of very short length due to the danger of an accident with such pressures. Liquid under such high pressures is not normally available in hospitals. In order to produce such a high liquid pressure, compressors or pumps can be used. However, known compressors or pumps are unsuitable for the intended medical purpose, since the liquid must be completely free of impurities, bacteria and air inclusions, i.e. the liquid must be completely sterile. This sterility is unavailable if known compressors or pumps are used in order to pump the liquid from a storage container to the catheter.

SUMMARY OF THE INVENTION

The object of the present invention is to provide a device by which sterile liquid in a pressure range of between 2 bar and 130 bar can be fed to the catheter in the required amount, sterile, and without air bubbles, so that a sharp liquid jet is emitted from the catheter. The liquid jet separates an organ part or a foreign body in a human or animal organ and/or crushes it into small pieces. Then this same liquid jet flushes the separated and crushed particles out of the organ through the same catheter. It should be possible to manufacture the device at low price as a mass produced article for a large number of possible uses. Furthermore, the device should be capable of simple use without need for specially trained personnel.

This object is achieved in accordance with the invention comprising a high pressure liquid dispenser for delivering preferably sterile liquid at high pressure to a catheter. The dispenser includes a flexible or weak wall storage container in which the liquid to be dispensed is stored and a conduit from the front end wall of that container for dispensing liquid to a catheter. A pressure container around the storage container is stiff enough to take up the pressure of the liquid and the possible deformation of the storage container, so that the pressure of the liquid elevated by a pump piston may be substantially greater than without the pressure container around the storage container. A fluid actuated drive acts on the pump piston. The piston of the fluid actuated drive and the pump piston are respectively so shaped as to provide a pressure boost for producing higher pressure in the liquid in the storage container to produce the jet.

There are a number of special features of the invention. It uses a storage container which, before its use, contains the liquid in sterile form and is completely closed. The liquid is forced out of the storage container by a pump action instead of by suction. It uses a compressed air network customarily available in hospitals to supply the drive energy for forcing the liquid out of the storage container. A pressure converter is used which, from the low pressure of between 2 and 10 bars of the compressed air, produces a pressure which is 2 to 20 times greater in the sterile liquid of the storage container. The storage container is supported by a pressure container to counteract the pressure exerted by the liquid on the storage container such that a commercial storage container, for instance, in the form of an ordinary plastic syringe, can be used. The liquid is stored without pressure in that container prior to its use. But, upon use, the high pressure is used. The high pressure presses the elastic walls of the storage container against the walls of the pressure container. As a result, the high pressure of the liquid is not substantially taken up by the storage container, which serves only as pressure-transfer element but instead by the pressure container so that the storage container need not be particularly resistant to pressure. The pressure of the liquid is controlled by controlling the pressure of the compressed air via electrically actuated compressed air valves operated by a microcomputer. The liquid is separated from the electric part of the valves by the compressed air part of the pressure converter. The liquid pressure can be regulated as a function of a predetermined desired pressure value or of a desired pressure-value curve and a given period of time, which are stored in the microcomputer, or as a function of the blood pressure or liquid pressure in the organ treated, at the place of treatment by a control device containing the microcomputer. The control device is used together with a catheter which has a liquid jet nozzle, a receiving opening which receives the liquid jet of the nozzle, a short cylindrical flow calming channel section downstream of the receiving opening and, adjoining it, a diffuser section which widens in the direction of flow and to which there can be connected a discharge line for the discharge of the stream consisting of liquid and the particles separated from or crushed from the human or animal organ.

Other objects, features and advantages of the present invention will become apparent from the following description of the invention which refers to the accompanying drawings.

DESCRIPTION OF THE PREFERRED EMBODIMENTS

Figure 1:
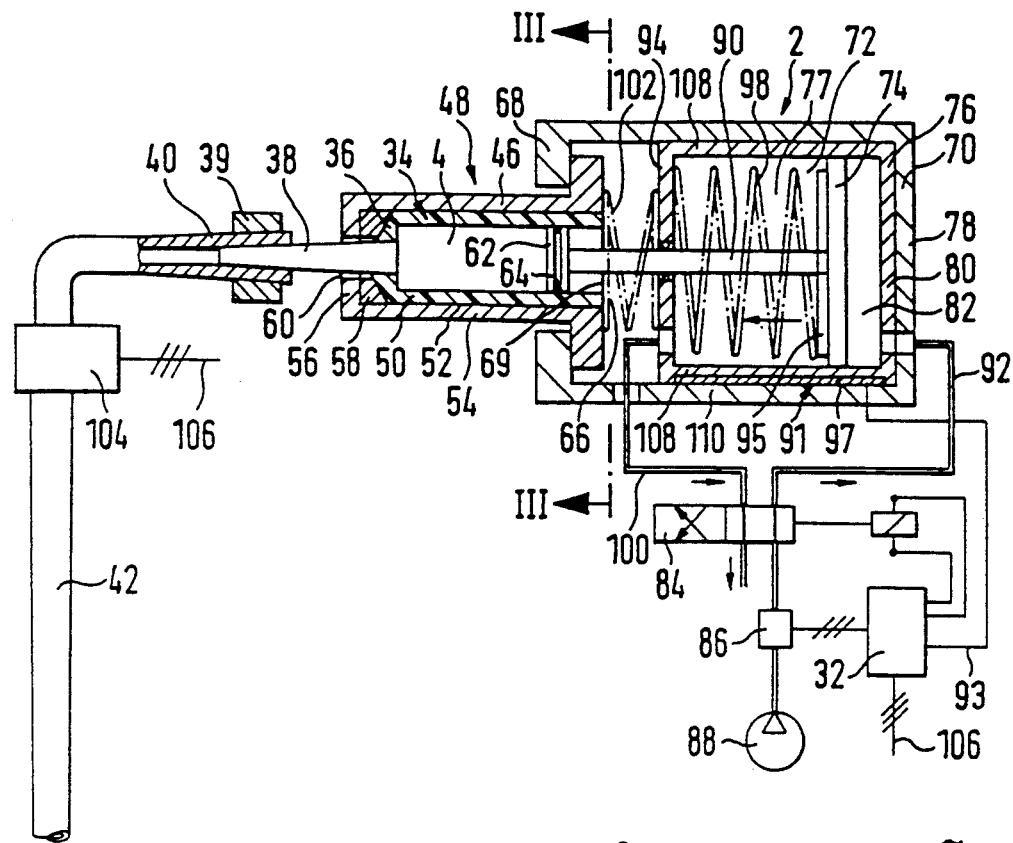
FIG. 1 is a showing, not to scale, generally in longitudinal direction, through a high-pressure liquid dispenser according to the invention, applied to a special catheter.
Figure 2:
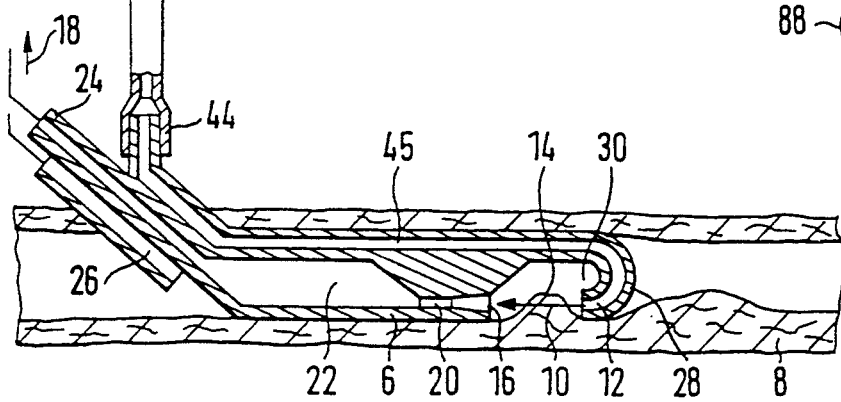
FIG. 2 shows a different switch position of an electrically actuatable valve for compressed-air control shown in FIG. 1.
Figure 3:
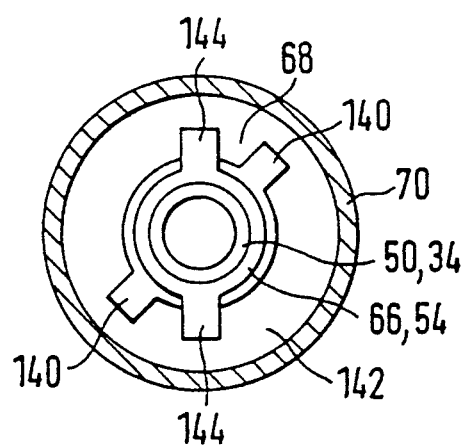
FIG. 3 is a cross-sectional view along the plane III—III of FIG. 1.

In FIGS. 1, 2 and 3, the individual parts have not been shown to scale in order that essential details can be more clearly recognized. FIG. 1 shows a blood path 8, for instance an artery or vein of a person or an animal. A catheter 6 is inserted in the blood path. These items are shown greatly enlarged. A storage container 34 containing sterile liquid 4 is shown on a greatly reduced scale as compared with the blood path. Blood paths such as arteries and veins are, on average, only a few millimeters thick. The size of the storage container 34 is large enough to contain at least ¼ liter, and preferably ½ liter, 1 liter, 2 liters, 5 liters, 10 liters or even more of sterile liquid. If the storage container 34 is of smaller capacity, it must be replaced too frequently with a new storage container with sterile liquid during a given operation.

The high pressure liquid dispenser 2 shown in FIGS. 1, 2 and 3 serves for dispensing sterile liquid 4 at such high pressure to the catheter 6 that the liquid 4 emerges from a nozzle 12 of the catheter 6 in the form of a sharp liquid jet 10. The organ 8 being served can, for instance, be a blood path, heart, muscle, liver, kidney, bladder, etc. of a human being or animal. The sharp jet results from high pressure and a small jet cross section without dispersion. The liquid jet 10 separates organ parts 14 in the organ 8 and crushes them (or, in the event foreign bodies are present, it crushes the foreign bodies present in the organ 8, for instance, kidney stones or gallstones). The liquid jet 10 entrains the separated and/or crushed particles together with the liquid and directs them into a collection opening 16. From there the particles are conducted through the catheter 6 out of the organ 8 in the direction indicated by an arrow 18. In the pathway through the catheter 6, downstream of the collecting opening 16, there are formed, one after the other, a short, narrow cylindrical flow calming channel section 20 and, adjoining it, a diffuser section 22 which expands in the direction of flow to a discharge conduit 24. The diffuser section 22 produces increased suction on the collection opening 16, and the suction draws the particles separated or crushed by the liquid jet 10 with strong suction into the liquid jet and, together with it, into the collecting opening 16. A pressure sensor 26, which is preferably a part of the catheter 6, can measure the pressure in the treated organ 8 at a selected point, for instance, as shown in FIG. 1, at the rear end of the catheter 6 or in front of the curved front end 28 having the nozzle 12 or in a space 30 in the catheter 6 between the curved front-end part 28, the collecting opening 16, and the liquid jet 10. The sensor 26 imparts an electrical pneumatic signal corresponding to the measured pressure to an electronic control device 32, which preferably contains a microprocessor and which can control the pressure of the liquid 4 as a function of the measured pressure value of the sensor 26.

The high pressure liquid dispenser 2 contains a substantially cylindrical storage container 34 which contains the sterile liquid 4. It is provided on its front end wall 36 with conduit connecting means 38. The storage container 34 is comprised of elastic material, preferably plastic. It is preferably a commercial medical syringe barrel. The conduit connecting means 38 is preferably comprised of a length of tube 38 which is conically tapered downstream on its surface and is customarily used with syringe barrels, such as a so called Luer cone (named after its inventor Luer). One end 40 of a fluid conduit 42 is connected to the conduit connecting means 38. The other end 44 of the conduit 42 is connected to a feed channel 45 of the catheter 6 which leads to the nozzle 12. The storage container 34 is of self-supporting stiffness, but it is easily flexible. It is known in medicine to place an injection needle instead of the conduit end 40 on the length of tube 38. A holding device 39, preferably a commercial Luer lock, is preferably provided. It prevents unintended separation of the plug connection of the tube length 38 with the conduit end 40. The holding device 39 can be a bayonet lock or some other rapidly locked and opened device. Instead of a conical tubular piece 38, a cylindrical tubular piece can be used. It is important that it be a part which is customarily used in medicine.

The storage container 34 can be inserted in a replaceable manner in a completely surrounding pressure cylinder 46 of a pressure container 48. The cylinder 46 so supports the peripheral wall of the storage container 34 against the pressure of the liquid 4 therein that an essential part of the pressure of the liquid 4 is transmitted through the wall of the storage container 34 to the wall of the pressure cylinder 46. In this way, the pressure level of the liquid 4 in the storage container 34 can be several times greater without the storage container 34 bursting or leaking than the pressure level of the liquid 4 at which the storage container 34 would burst or leak without the protection of the pressure cylinder 46. For this purpose, the end wall 36 and the cylindrical wall 50 of the storage container 34 must be flexible and rest either directly or via intermediate elements against the walls defining the cylindrical space 52 of the pressure cylinder 46. In the embodiment shown, the cylindrical wall 50 of the storage container 34 rests directly against the inside of the cylindrical wall 54 of the pressure cylinder 46. The end wall 36 of the storage container 34 is conical on the outside and the end wall 56 of the pressure cylinder 46 which lies opposite it is flat. For adapting these different shapes, a pressure ring 58 is inserted between these two front end walls 36 and 56. It is adapted in form at its two ends to the front end walls 36 and 56. In this way, the pressure ring 58, over its entire cross sectional size, transmits the pressure of the liquid 4 from the storage container 34 to the end wall 56 of the pressure cylinder 46. The cylindrical wall 50 of the storage container 34 lies essentially over its entire length against the cylindrical wall 54 of the cylindrical space 52 of the pressure cylinder 46 so that the pressure of the liquid 4 is transmitted directly through the cylindrical wall 50 of the storage container 34 to the cylindrical wall 54 of the pressure cylinder 46. The syringe needle 38 extends through central holes 60 in the pressure container end wall 56 and the pressure ring 58.

The storage container 34 can be comprised of a brittle material, such as glass. In that case, all pressure transmitting surfaces between the storage container 34 and the pressure cylinder 46 must lie firmly against each other so that the storage container 34 does not burst or crack upon the high pressures of the liquid present in it. This makes more difficult the required possibility of replacing an empty storage container 34 with a new full one. Alternatively an empty storage container 34 must be replaced together with the pressure cylinder 46, since they are firmly engaged in each other. However, this is expensive. Therefore, in the preferred embodiment of the invention, the storage container 34 is comprised of plastic. Plastic is more elastic than glass. A storage container 34 of plastic can be more easily inserted axially into the cylindrical space 52 of the pressure cylinder 46 if the two have the same diameter. Furthermore, in order to facilitate the insertion and replacement of the storage container, the storage container 34 may have a diameter which is a few hundredths or tenths of a millimeter smaller than the cylindrical space 52 which receives it. This slight difference in diameters does not lead to bursting or leaking of the storage container 34 of plastic because under the pressure of the liquid 4, the container can expand elastically a very small amount which, however, is sufficient for a firm pressure contact with the cylindrical wall 54 of the pressure cylinder 46 and its end wall 56. Upon such expansion, the storage container 34 must not spring a leak of the liquid 4 between its cylindrical wall 50 and a pump piston 62 which is guided axially in the wall 50. The piston 62 can be a piston which is customarily used for syringes and which is preferably provided with an elastic annular seal 64. The pump piston 62 is preferably comprised of plastic. The pressure cylinder 46 is open at the end 66 facing away from its end wall 56 so that the storage container 34 and the piston pump 62 can be inserted through this open end 66 into the pressure cylinder 46 and so that when the storage container 34 is empty, it can be replaced by a new storage container 34 filled with liquid 4 possibly also along with another pump piston 62.

A pressure cylinder head 70 of the pressure container 48 is detachably fastened via a rapid closure, for instance a so-called bayonet lock 68, to the open end 66 of the pressure cylinder 46. The head 70 forms an axial extension of the pressure cylinder 46 and has a larger diameter. A fluid actuating drive 72 is arranged within the pressure cylinder head 70. It can press the pump piston 62 in the direction from the rear end 69 of the storage container 34 up to its front end wall 36. As long as the storage container 34 is held ready to supply liquid, the pump piston 62 rests against the pool of liquid 4 without exerting any substantial pressure on the liquid. During use, the liquid 4 is to be delivered to the catheter 6. The fluid actuating drive 72 then presses the pump piston 62 with enough pressure against the liquid 4 within the storage container 34 that a pressure is produced in the liquid, and depending on the purpose of use, that pressure may lie between 2 bars and 130 bars. With a lower pressure, the liquid jet 10 in the catheter 6 would no longer have the desired effect. Pressures of even more than 130 bar can also be produced. But such higher pressures do not appear necessary for the described action of the liquid jet 10.

The fluid actuating drive 72 contains a piston-cylinder unit having a drive piston 74 and a drive cylinder 76 within which the drive piston 74 is axially guided. The drive cylinder 76 rests on the rear end wall 78 of the pressure cylinder 70 facing away from the rapid fastener 68. It forms an expandable work cylinder space 82 between the drive piston 74 and the rear end wall 80 of the drive cylinder 76. The cylinder space 82 can be connected via a valve 84 and a pressure regulator 86 to a source of compressed gas 88. The compressed gas, which is preferably compressed air, from the source of compressed gas 88 presses the drive piston 74 and the pump piston 62 of the storage container 34, which is rigidly connected to it via a piston rod 90, in the direction toward the front end wall 36 of the storage container 34. It is only by the pressure of the drive piston 74 on the pump piston 62 that the high pressure of 2 bar to 130 bar of the liquid 4 is produced in the storage container 34. The drive piston 74 and the drive cylinder 76 have a substantially larger active cross section, which is acted on by compressed air in the pressure space 82, than the cross section of the pump piston 62 and the storage container 34. As a result, the drive piston 74 and the drive cylinder 76 on the one hand and the pump piston 62 and the storage container 34 on the other hand together from a pressure converter which converts a low pneumatic pressure in the pressure space 82 to a pressure in the liquid 4 in the storage container 34 which is between two and three times higher. As a result, it is sufficient for the gas pressure at the source of compressed gas 88 and in its conduit 92 to the pressure space 82 to be substantially less, so that it amounts, for instance, only to 2 bar to 5 bar. Thus, no risk or only a slight risk of accident exists for the pneumatic part and particularly pressure resistant elements are not required.

When the storage container 34 is completely empty, the pump piston 62 has moved to the front end wall 36 of the storage container 34, and the drive piston 74 is near a front end wall 94 of the drive cylinder 76. Both pistons 62 and 74 can be moved back into their positions shown in FIG. 1 by a compression spring 98 which is arranged in the drive cylinder 76. The cylindrical space 77 between the front end wall 94 of the drive cylinder 76 and the drive piston 74 can be vented into the open atmosphere or can be alternately vented or connected to the source of compressed gas 88 through a fluid line 100 via the valve 84. FIG. 1 shows the position of the valve 84 in which the operating cylindrical space 82 is acted on by compressed air and the opposite cylindrical space 77 is vented. FIG. 2 shows the valve 84 in a position in which the source of compressed gas 88 is connected to the cylindrical space 77 and the operating pressure space 82 is vented so that the gas pressure of the source of compressed gas 88 can move the two pistons 62 and 74, instead of the compression spring 98, back into the positions shown in FIG. 1.

For positioning the drive cylinder 76 on the rear end wall 78 of the pressure cylinder head 70, a compression spring 102 is arranged between the front end wall 94 of the drive cylinder 76 and the rear end 66 of the pressure cylinder 46.

Certain desired pressure values of the liquid 4 can be stored in the electronic control device 32 so that the electronic control device 32 can regulate the pressure of the liquid 4 via the pressure regulator 86, as a function of an actual pressure level which is measured in the storage container 34, or the conduit 42 or in the catheter 6, and which is communicated automatically to the electronic control device 32. Instead of a fixed desired pressure level, desired pressure level curves can be stored in the electronic control device 32. The pressure of the liquid 4 is varied as a function of the pressure curves and regulated over given periods of time. Independently of these two types of regulation, or in addition to them, the pressure of the liquid 4 and/or the speed of conveyance of the liquid 4 can be set or regulated as a function of the organ pressure measured by the sensor 26 in the organ 8.

If the pressure cylinder head 70 and the drive cylinder 76 are at least partially transparent, then the instantaneous position of the drive cylinder 74 is visible from the outside. A position measuring device 91 is preferably provided. Via electric lines 93 and by means of electric signals, it indicates the axial position at the time of the drive piston 74 with respect to the drive cylinder 76. These electric signals can produce an optical indication of the axial position at the time of the drive piston 74, which is equivalent to the position of the pump piston 62, and/or it can be used by the electronic control device 32 for the time-dependent and/or pressure-dependent adjustment or control i.e pressure of the treatment liquid 4 and/or pressure in the patient or in the organ 8 treated, of the advancing movement of the drive piston 74 and of the pump piston 62. For this, a desired level or desired level curves can be stored in the control device 32. The position measuring device 91 can comprise of a signal transmitter 95 fastened to the drive piston 74, for instance a permanent-magnet ring, and of a sensor 97 which notes its axial position, for instance an electric magnetic-field sensor, to which the line 93 is connected. This is a so-called inductive path measuring device.

For certain uses, it is advantageous if the liquid jet 10 is not a continuous flow jet but instead a liquid jet which pulsates at a frequency with high pressure. For this purpose, the compressed gas of the compressed-gas source 88 can be fed in a pulsating manner to the pressure space 82. In a preferred embodiment, a pulsator 104 is inserted in the conduit 42 between the storage container 34 and the catheter 6. The pulsator is controlled by the electronic control device 32 via electric lines 106 and it superimposes a pressure pulsation on the pressure of the liquid 4 in the conduit 42. This "superimposing" can be effected in the manner that the pulsator 104 alternately narrows or closes and reopens the cross section of flow of the conduit 42 at a given point with the desired pulsation frequency.

The valve 84 for the fluid actuating drive 72 is preferably actuated electrically by the electronic control device 32.

The pressure container 48, the fluid actuating drive 72, and the storage container 34 together form a handy structural unit. For replacement of an emptied storage container 34 with a filled one, it is merely necessary to separate the pressure cylinder 46 and the cylinder head 70 of the pressure container 48 from each other at the rapid closure 68. They preferably are comprised of metal. In a separated state, the storage container 34 can be pulled out of the pressure cylinder 46 through its open rear end 66. If necessary, the pressure ring 58 can also be replaced in this way. The drive cylinder 76 may be comprised of metal or plastic. The drive cylinder 76, similarly to the storage container 34, may be comprised of a material of such thin walls that it merely withstands the pneumatic pressure produced in the pressure space 82 without leaking or bursting when, as shown in FIG. 1, it rests via its rear end wall 80 and its cylindrical wall 108 against the read end wall 78 and the cylindrical wall 110 of the pressure cylinder head 70. In that case, the head 70 takes up the pressure from the pressure space 82, and the corresponding walls of the drive cylinder 76 are merely pressure transmitting intermediate elements.

FIG. 3 shows a possible embodiment of the rapid closure 68 which can be formed by radial recesses 140 in the front end wall 142 of the pressure cylinder head 70 and radial projections 144 on the rear end 66 of the pressure cylinder 46, or vice versa. The radial projections 144 can pass axially through the radial openings 140 and then be rotated to such an extent relative to these openings that they rest axially against the adjacent regions of the end wall 142 of the pressure cylinder head 70.

All parts of the storage container 34 and of the pressure cylinder 46 preferably have a circular cross sectional shape.

In the embodiment shown in FIG. 1, the storage container 34 serves as pump cylinder in which the pump piston 62 is guided axially in liquid tight manner. In its unused condition, the liquid 4 is filled in sterile manner in the storage container 34, but substantially without pressure, and the pump piston 62 serves as a closure element for the storage container 34.

Figure 4:
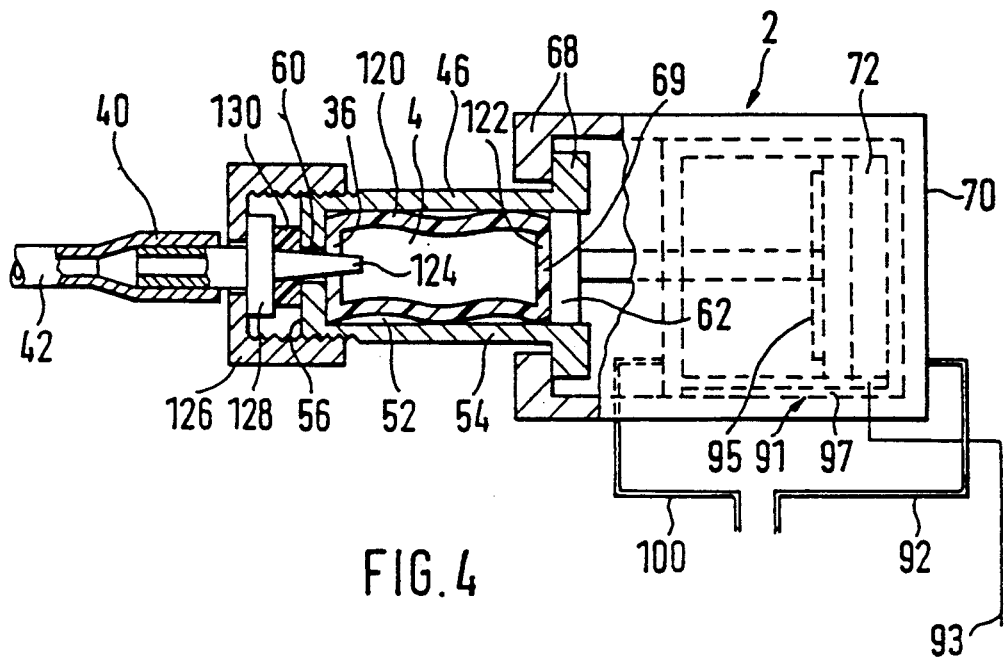
FIG. 4 shows another embodiment, partially in longitudinal section, of a high-pressure liquid dispenser according to the invention.

In the further embodiment of a high pressure liquid dispenser shown in FIG. 4, all parts are the same as in FIG. 1 with the following exception. The storage container 120 for the liquid 4 is not a self-supporting, rigid body but instead is a container which can be collapsed by a pump piston 62 which presses against its rear end wall 122. The front end wall 36 of this collapsible container, which is preferably formed of plastic, can be provided with a syringe needle 38 corresponding to that in FIG. 1 or can be developed as a conduit connecting means so that it can be punctured by a hollow needle 124 which is connected with the upstream end 40 of the conduit 42. For this purpose, a screw cap 126 can be screwed onto the cylinder wall 54. It forces the hollow needle through the front end wall 36 by means of an annular collar 128. Between the annular collar 128 and the front end wall 56 of the pressure cylinder 46, there is preferably a seal 130 which seals off the hole 60. The pump piston 62 is guided axially in the pressure cylinder 46 and rests displaceably, but in a fluid tight manner, against the cylindrical wall 54 the cylinder 46.

In the embodiment of FIG. 4, the pressure cylinder 46 serves as a pump cylinder within which the pump piston 62 is axially guided in a fluid tight manner.

In a modified embodiment, instead of the source of compressed gas 88 which supplies the compressed gas, a source of pressurized liquid 88 could be provided, which supplies a liquid having a pressure of between 2 bar and 10 bar into the work pressure chamber 82 of the fluid actuating drive 72. In the chamber 82, the pressure liquid acts on the drive piston 74 and, via the pump piston 62, the pressure compresses the liquid 4 in the storage container 34 to a pressure of between about 6 bar and 130 bar.

In accordance with a preferred embodiment of the invention, the liquid 4 is driven into the catheter 6 at a pressure within the range of 48 bar (about 600 p.s.i.) and 60 bar (about 900 p.s.i.) from the pump piston 62 out of the storage container 34.

The use of a surrounding stiff pressure container 48 has the advantage that the replaceable storage container 34 need not be particularly resistant to pressure and therefore can be manufactured economically, and preferably of plastic. As an article mass produced in large numbers, storage containers can be filled, sterilized with the liquid inside, and transported and stored with this liquid. During this time, the liquid in the storage container may be without pressure, or be under a vacuum or be under only a slight pressure. The storage container 34 can even be an ordinary commercial medical syringe cartridge. The pressure container 48 can be used successively for a large number of storage containers 34.

If there is available a source of pressure fluid 28 which supplies the pressure fluid under a sufficiently high pressure, the drive piston 74 and the pump piston 62 need not form a pressure booster with each other. In this case, the cross-sectional area of the drive piston 74 can be equal to or less than the cross-sectional area of the pump piston 62. The disadvantage of this design is that the pressure fluid conduit 92 and its conduit connections must be developed sufficiently pressure resistant for the high pressure. In all cases, the pressure fluid may be pressurized liquid but it is preferably compressed air. Highly reliable operation without the danger of pressure fluid passing into the sterile liquid 4 in the storage container 34 is established because the pressure fluid of the pressure-fluid source 88 is not separated from the sterile liquid 4 merely by the pump piston 62 but is also separated by the drive piston 74.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A high pressure liquid dispenser for dispensing sterile liquid in the form of a liquid jet, the dispenser comprising:

a pressure container having an open space therein, the pressure container being resistant to a high, liquid dispensing pressure; the pressure container having an interior of particular shape, a storage container replaceably disposed inside the pressure container and shaped externally generally to the shape of the interior of the pressure container; the storage container being deformable under pressure, and the pressure container being sufficiently stiff for preventing deformation of the storage container upon pressure being applied thereto, a pump piston in the pressure container and disposed against the storage container in the pressure container; pressure application means for applying pressure to the pump piston;

the internal pressure resisting strength of the storage container being substantially below the internal pressure resisting strength of the pressure container; the liquid being storable at a pressure in the storage container which is substantially below the pressure applied to the storage container by the piston when the storage container is in the pressure container;

a catheter connected to the storage container through the pressure container, the catheter extending to a jet outlet to which the liquid is to be dispensed under pressure, and the pump piston being operable by the pressure application means for pressing upon the storage container for urging the storage container into engagement with the interior of the pressure container so that the pressure container can take up the high pressure caused deformation of the storage container which is produced by the pressure of the pump piston on the storage container.

2. The dispenser of claim 1, wherein the catheter includes a collection opening which is separate from the liquid being dispensed, the jet outlet from and the collection opening of the catheter being spaced apart but being so positioned that liquid exiting from the jet outlet is collected with other material which may be collected or produced by the jet in the collection opening of the catheter.

3. The dispenser of claim 1, wherein the pressure application means comprises means for applying fluid pressure for operating the pump piston.

4. The dispenser of claim 1, wherein the storage container is substantially cylindrical in shape; the storage container having a front end toward the catheter, and conduit connecting means at the front end, the conduit connecting means being connectable with the catheter for delivering liquid under high pressure to the catheter.

5. The dispenser of claim 1, wherein the storage container inside the pressure container transmits pressure on the liquid in the storage container, while the pressure container, with which the storage container is in contact, opposes the pressure in the storage container, whereby the pressure in the storage container while under pressure from the pump piston in the pressure container can be several times higher than the pressure at which the storage container would burst or leak without the storage container being contained in and protected by the pressure container.

6. The dispenser of claim 4, wherein the pump piston is supported in the pressure container to move axially along the pressure container and toward the front end of the storage container for delivering liquid through the front end conduit connecting means to the catheter.

7. The dispenser of claim 4, wherein the pressure application means comprises a piston-cylinder unit including: a drive cylinder, a drive piston axially displaceable in the drive cylinder, one of the cylinder and the piston being moveable and being connected with the pump piston for moving the pump piston in the direction for pressurizing the storage container.

8. The dispenser of claim 7, wherein the drive piston and the pump piston together form a pressure booster, wherein the surface area of the drive piston acted upon by pressure fluid is substantially greater than the surface area of the pump piston acting on the liquid in the storage container.

9. The dispenser of claim 8, wherein the difference in surface area between the drive piston and the pump piston are selected so that a liquid pressure about 30 times higher than the liquid pressure in the drive cylinder is developed in the storage container, from a low pressure value of 2 bar to 10 bar in the drive cylinder of the pressure application means.

10. The dispenser of claim 8, wherein the pressure application means is compressed air fluid actuated.

11. The liquid dispenser of claim 7, further comprising a fluid feed to the pressure application means, and an electrically actuated valve on the fluid feed from the jet for controlling the pressure thereto, an electronic control device with a microcomputer operating on the electrically actuated valve for maintaining a desired pressure level in the pressure application means through the fluid feed.

12. The dispenser of claim 7, wherein the pressure applications means is also arranged in the pressure container forming a structural unit with the pressure container.

13. The dispenser of claim 1, wherein the pressure container has an opening therein for enabling removal and replacement of the storage container in the pressure container; a closure for the opening of the pressure container.

14. The dispenser of claim 4, wherein the pressure container has a front end wall which is opposed to and cooperates with the front end of the storage container;

a pressure plate disposed between the front end of the storage container and the front end wall of the pressure container, the pressure plate having opposite surfaces with shapes adapted to the shapes of the front end and front end wall in order to lie against each other.

15. The dispenser of claim 1, wherein the pressure container has a compressive strength that is several times greater than that of the storage container.

16. The dispenser of claim 15, wherein the storage container is comprised of plastic.

17. The dispenser of claim 16, wherein the pressure container is comprised of metal and is stiffer than the storage container.

18. The dispenser of claim 16, wherein the storage container is comprised of a syringe barrel of a commercial medical syringe.

19. The dispenser of claim 18, wherein the pump piston comprises a commercial medical syringe piston, the pressure chamber is defined by a cylindrical wall shaped to the shape of the syringe piston so that the syringe piston engages the cylindrical wall in the pressure container in a pressure tight manner and is axially displaceable therein against the storage container.

20. The dispenser of claim 4, wherein the conduit connecting means comprises a hollow, externally conical length of tube, and the tube having a channel in flow communication with and extending through the front end of the storage container.

21. The dispenser of claim 20, further comprising a conduit having an end placeable on the conduit connecting means, and a locking device for securely holding the conduit end on the conduit connecting means tube.

22. The dispenser of claim 1, wherein the pressure container is comprised of metal and is stiffer than the storage container.

23. The dispenser of claim 1, further comprising means for causing pressure pulsation of the liquid as the liquid is delivered from the storage container through the catheter.

24. The dispenser of claim 1, wherein the pressure container is generally cylindrically shaped with cylindrical inner surfaces, and the pump piston is arranged in the cylindrical space of the pressure container for movement therealong.

25. The dispenser of claim 24, wherein the storage container is an axially collapsible bag in the pressure container which is filled with liquid and which rests in a pressure transmitting manner against the interior of the pressure container, and the pump piston in the pressure container presses axially against the flexible bag for pressurizing the bag.

26. The dispenser of claim 25, wherein the storage container is an axially collapsible bag comprised of plastic.

* * * * *